(12) United States Patent
Van Kranenburg et al.

(10) Patent No.: US 8,497,128 B2
(45) Date of Patent: Jul. 30, 2013

(54) GENETIC MODIFICATION OF HOMOLACTIC THERMOPHILIC BACILLI

(75) Inventors: Richard Van Kranenburg, Wageningen (NL); Mariska Van Hartskamp, Gorinchem (NL); Eelco Anthonius Johannes Heintz, Gorinchem (NL); Esther Johanna Geertruda Van Mullekom, Druten (NL); Jurgen Snelders, Bemmel (NL)

(73) Assignee: Purac Biochem B.V., Gorinchem (NL)

( * ) Notice: Subject to any disclaimer, the term of this patent is extended or adjusted under 35 U.S.C. 154(b) by 1286 days.

(21) Appl. No.: 12/087,652

(22) PCT Filed: Jan. 24, 2007

(86) PCT No.: PCT/EP2007/000623
§ 371 (c)(1),
(2), (4) Date: Sep. 23, 2008

(87) PCT Pub. No.: WO2007/085443
PCT Pub. Date: Aug. 2, 2007

(65) Prior Publication Data
US 2010/0009420 A1   Jan. 14, 2010

Related U.S. Application Data

(60) Provisional application No. 60/761,336, filed on Jan. 24, 2006.

(30) Foreign Application Priority Data

Jan. 24, 2006  (EP) ..................................... 06100778
Mar. 23, 2006  (EP) ..................................... 06111636

(51) Int. Cl.
*C12N 15/75*     (2006.01)
*C12N 15/74*     (2006.01)
*C12N 15/00*     (2006.01)
*C12N 1/21*      (2006.01)

(52) U.S. Cl.
USPC .... 435/485; 435/471; 435/320.1; 435/252.31

(58) Field of Classification Search
USPC .......................... 435/471, 485, 320.1, 252.31
See application file for complete search history.

(56) References Cited

U.S. PATENT DOCUMENTS

| | | | |
|---|---|---|---|
| 5,171,673 A | 12/1992 | Sloma et al. | |
| 5,919,678 A | 7/1999 | Gruss et al. | |
| 2002/0042134 A1 | 4/2002 | Green et al. | |
| 2004/0029256 A1* | 2/2004 | Rajgarhia et al. | 435/254.2 |

FOREIGN PATENT DOCUMENTS

| | | | |
|---|---|---|---|
| EP | 1 437 415 A1 * | 7/2004 | |
| JP | A-2004-510435 | 4/2004 | |
| WO | WO 02/14490 A2 | 2/2002 | |
| WO | WO 02/29030 A2 | 4/2002 | |
| WO | WO 2004/063382 A2 | 7/2004 | |
| WO | WO 2005/086670 A2 | 9/2005 | |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Biswas et al., Journal of Bacteriology 175(11):3628-3635, 1993.*
Platteeuw et al., Applied and Environmental Microbiology 60(2):587-593, 1994.*
Hayes et al., Applied and Environmental Microbiology 56(1):202-209, 1990.*
Bernard et al., FEBS Letters 290(1-2):61-64, 1991.*
Outtrup et al., "Chapter 14: The importance of *Bacillius* Species in the Production of Industrial Enzymes", *Applications and Systematics Bacillus and Relatives*, 2002, pp. 206-218.
Ball et al., "Properties of protoplasts from the thermophile *Bacillus coagulans* and their significance for genetic studies", *Letters in Applied Microbiology*, vol. 9, 1989, pp. 141-144.
Bulthuis et al., "Formation of fermentation products and extracellular protease during anaerobic growth of *Bacillus licheniformis* in chemostat and batch-culture", *Antonie van Leeuwenhoek*, vol. 60, 1991, pp. 355-371.
Mann et al., "Transformation of *Bacillus* supp.: An Examination of the transformation of *Bacillus* protoplasts by plasmids pUB110 and pHV33", *Current Microbiology*, vol. 13, 1986, pp. 191-195.
Simon et al., "Construction of a vector plasmid family and its use for molecular cloning in *Streptococcus lactis*", *Biochimie* vol. 70, 1988, pp. 559-566.
Burdett, "Identification of Tetracycline-Resistant R-Plasmids in *Streptococcus agalactiae* (Group B)", *Antimicrobial Agents and Chemotherapy*, vol. 18, No. 5, Nov. 1980, p. 753-760.
Zeigler, "The genus *Geobacillus*: introduction and strain catalog", *Bacillus Genetic Stock Center, Catalog of Strains*. 7th Edition, vol. 3, 2001.
Haima et al., "The effect of restriction on shotgun cloning and plasmid stability in *Bacillus subtilis* Marburg" Mol. Gen. Genet., vol. 209, 1987, pp. 335-342.
O'Sullivan et al., "Rapid Mini-Prep Isolation of High-Quality plasmid DNA from *Lactococcus* and *Lactobacillus* spp.", *Applied and Enviromental Microbiology*. vol. 59, No. 8, Aug. 1993, pp. 2730-2733.

(Continued)

*Primary Examiner* — Delia Ramirez
(74) *Attorney, Agent, or Firm* — Oliff & Berridge, PLC

(57) ABSTRACT

Disclosed herein is a genetic modification of moderately thermophilic *Bacillus* species that are facultative anaerobic and homolactic. The method includes introducing DNA cloned in a thermosensitive plasmid system containing a pSH71 replicon or a homologue thereof into cells of a moderately thermophilic *Bacillus* species that is facultative anaerobic and homolactic; culturing the cells on a selective medium at a permissive temperature to select transformed cells; culturing the transformed cells on a selective medium at a non-permissive temperature to select transformed cells capable of growing on the selective medium at the non-permissive temperature. The method can modify the Bacilli for R-lactic acid production, production of other organic acids than lactic acid, alcohol, enzymes, amino acids, and vitamins. The *Bacillus* species may be modified by replacing the S-lactate dehydrogenase gene by a DNA construct including a DNA sequence encoding R-lactate dehydrogenase.

11 Claims, 7 Drawing Sheets

OTHER PUBLICATIONS

Platteeuw et al., "Use of the *Escherichia coli* β-Glueuronidase (gusA) Gene as a Reporter Gene for Analyzing Promoters in Lactic Acid Bacteria", *Applied and Environmental Microbiology*, vol. 60., No. 2, Feb. 1994, pp. 587-593.

Kiewiet et al., "The Mode of Replication Is a Major Factor in Segregational Plasmid Instability in *Lactococcus lactis*", *Applied and Environmental Microbiology*, vol. 59, No. 2, Feb. 1993, pp. 358-364.

Platteeuw et al., "Characterization and heterologous expression of the *tetl*. gene and identification of *iso* ISS / elements from *Enterococcus faecalis* plasmid pJH1", *Gene*, vol. 160., 1995, pp. 89-93.

Keggins et al., "Molecular cloning of genetically active fragments of *Bacillus* DNA in *Bacillus subtilis* and properties of the vector plasmid pUB110", *Proc. Natl. Acad. Sci. U.S.A.*, vol. 75, No. 3, Mar. 1978, pp. 1423-1427.

Kranenburg et al., "Functional Analysis of Three Plasmids from *Lactobacillus plantarum*", *Applied and Environmental Microbiology*, vol. 71, No. 3, Mar. 2005, pp. 1223-1230.

Trieu-Cuot et al., "Plasmid transfer by conjugation from *Escherichia coli* to Gram-positive bacteria", *FEMS Microbiology Letters*, vol. 48, 1987, pp. 289-294.

Namy et al., "Co-existence of *clpB* and *clpC* in the Bacillaceae", *FEMS Microbiology Letters*, vol. 173, 1999, pp. 297-302.

Bernard et al., "Cloning of the D-Lactate dehydrogenase gene from *Lactobacillus delbrueckii* subsp. *bulgaricus* by complementation in *Escherichia coli*", *FEBS Letters*, Elsevier, Amsterdam, vol. 290, 1991, pp. 61-64.

Bernard et al., "NAD$^+$-dependent D-2-hydroxyisocaproate dehydrogenase of *Lactobacillus delbrueckii* subsp. *bulgaricus* Gene cloning and enzyme characterization", *European Journal of Biochemistry*, vol. 224, 1994, pp. 439-446.

European Search Report issued in Patent Application No. 06111636. 4, on Nov. 13, 2006.

Fleming et al.; "Extracellular Enzyme Synthesis in a Sporulation-Deficient Strain of *Bacillus licheniformis*;" *Applied and Environmental Microbiology*; Nov. 1995; pp. 3775-3780; vol. 61, No. 11; American Society for Microbiology.

Sozhamannan et al.; "Plus-Origin Mapping of Single-Stranded DNA Plasmid pE194 and Nick Site Homologies with Other Plasmids;" *Journal of Bacteriology*; Aug. 1990; pp. 4543-4548; vol. 172, No. 8; American Society for Microbiology.

Petit et al.; "Tn10-Derived Transposons Active in *Bacillus subtilis;*" *Journal of Bacteriology*; Dec. 1990; pp. 6736-6740; vol. 172, No. 12; American Society of Microbiology.

David et al.; "Plasmid Transformation by Electroporation of *Leuconostoc paramesenteroides* and Its Use in Molecular Cloning;" *Applied and Environmental Microbiology*; Jun. 1989; pp. 1483-1489; vol. 55, No. 6; American Society for Microbiology.

Rygus et al.; "Catabolite Repression of the *xyl* Operon in *Bacillus megaterium;*" *Journal of Bacteriology*; May 1992; pp. 3049-3055; vol. 174, No. 9; American Society for Microbiology.

Vehmaanperä et al.; "Genetic manipulation of *Bacillus amyloliquefaciens;*" *Journal of Biotechnology*; Jul. 1991; pp. 221-240; vol. 19, No. 2; Elsevier B.V. (Abstract only).

Notice of Reasons for Rejection dated Jun. 1, 2012 from Japanese Patent Application No. 2008-551719 (translation only).

Rhee et al., Development of plasmid vector and electroporation condition for gene transfer in sporogenic lactic acid bacterium, *Bacilus coagulans*, Plasmid (2007), vol. 58, issue 1, pp. 13-22.

Bryan et al., Improved Vectors for Nisin-Controlled Expression in Gram-Positive Bacteria, Plasmid, (2000), vol. 44, pp. 183-190.

* cited by examiner

```
  1 AGATCTTGGT TCCCCACCTT TTTTACAGAC TTATCACTAT ATTATTATAG
 51 ATAAACCGGC CAAACAACCA AATCGGGGCG CAAAGGAGAG CCGGGGCGTG
101 GATTTAAACC ATTTTTGGAA AAACAAAAGG AAAACCTGCT TGTAAAAAGA
151 TGTTTTCGCG AAACGAAAGC GGGAATAGTA CCTTTGTTCT CTTCGCCTTT
201 TGTCATGCTT AAAATCATAA TTGATTGAAA ATTTTTTCAT GTTCACTTAT
251 ACTAAACGCA TCAACTATTA CTTCTTTTGG AAGGGGCAGT TTCCATGGGG
301 ATCC
```

Figure 3

GENETIC MODIFICATION OF HOMOLACTIC THERMOPHILIC BACILLI

The present invention relates to genetic modification for industrial applications of moderately thermophilic *Bacillus* species that are facultative anaerobic and homolactic.

Lactic acid and its salts, known as lactate, are commercially viable products useful in various fields including medicine, biodegradable polymers and food processing. Moderately thermophilic *Bacillus* species that are facultative anaerobic and homolactic are ideal organisms for the industrial manufacture of lactic acid. They are capable of growing at temperatures between 30-65° C. and allow anaerobic industrial fermentation at temperatures above 50° C. This high temperature has several advantages when fermenting on industrial scale: less risk of infections and thus higher enantiomeric purity, faster reactions etcetera. The homolactic nature allows the production of lactic acid from hydrocarbon sources (including hexose and pentose sugars; See WO 04/063382) without the formation of more than 15 wt % side products such as formic acid and acetic acid. The facultative anaerobic nature of the bacilli allows fermentation under anaerobic conditions, or at least under a low partial pressure of oxygen, which for Industrial scale is desirable because it allows for relatively inexpensive equipment and processing. Furthermore, the nutrient requirements of these bacteria are less demanding than those of lactic acid bacteria such as *Lactobacillus* species, which also allows for relatively inexpensive Industrial processes. One disadvantage of the known moderately thermophilic bacilli which are facultative anaerobic and homolactic is the fact that they do not or do virtually not produce R-lactate. Since successful application of biodegradable lactic acid polymers will depend on the availability of both inexpensive S-lactic acid and inexpensive R-lactic acid, a cost-effective production of both enantiomers is required. Presently known R-lactate-producing bacteria are either mesophilic (e.g. *Bacillus laevolacticus*) or have demanding nutrient requirements (e.g. *Lactobacillus delbrueckii*), which makes the manufacture of R-lactate much more expensive than that of S-lactate.

Thus, one object of the present invention is to avail of a moderately thermophilic *Bacillus* strain which is facultative anaerobic and produces R-lactic acid by homolactic fermentation. Another object of the invention is to avail of a method to produce genetically engineered moderately thermophilic bacilli which are facultative anaerobic and homolactic.

The genus *Bacillus* comprises over 200 different species (See Sneath, P. H. A., 1986: Endospore-forming Gram-positive rods and cocci. in Bergey's manual of systematic bacteriology. Vol 2. Sneath, P. H. A., Mair, N. S., Sharpe, M. E., Holt, J. G. (eds) Williams & Wilkins, Baltimore). Only a small fraction of these are known to be genetically accessible. For instance, protoplast transformation functions for a number of different *Bacillus* species, but transformation of competent cells has generally only been shown to work satisfactory for cells of the strictly aerobic and mesophilic *Bacillus subtilis* 168. Industrial strains are often more resistant to genetic modification as is known from *Bacillus licheniformis*. This facultative-anaerobic moderately thermophilic *Bacillus* species is used for the industrial production of enzymes. However, because of its heterolactic nature it cannot be used for the production of lactic acid (See Bulthuis, B. A., C. Rommens, G. M. Koningstein, A. H. Stouthamer, H. W. van Verseveld, 1991: *Formation of fermentation products and extracellular protease during anaerobic growth of Bacillus licheniformis in chemostat and batch-culture*, Antonie van Leeuwenhoek 60:355-371). In general, high-frequency competence transformation procedures are not available for industrial strains (See Outtrup, H., and S. T. Jørgensen, 2002: *The importance of Bacillus species in the production of industrial enzymes in Applications and systematics of Bacillus and relatives*. R. Berkeley, M. Heyndrickx, N. Logan, and P. de Vos (eds.), pp. 206-218, Blackwell Publishing, Malden, USA). Such strains may be modified by protoplast transformation as disclosed in U.S. Pat. No. 6,083,718.

To date, no methods demonstrating genetic engineering of moderately thermophilic *Bacillus* species that are facultative anaerobic and homolactic are described. Although one report has been published that claims plasmid transfer from *B. subtilis* to *Bacillus* coagulans by protoplast fusion (See Ball, A. S., and C. Edwards, 1989: *Properties of protoplasts from the thermophile Bacillus coagulans and their significance for genetic studies*. Lett. Appl. Microbiol. 9:141-144), it provides no evidence that the *B. coagulans* indeed harbours the plasmid. The claim is only based on the observation of growth of antibiotic-resistant colonies, which could very well have been spontaneous antibiotic-resistant mutants. We have observed such spontaneous antibiotic-resistant mutants of *B. coagulans* frequently for various types of antibiotics. In another publication: Transformation of *Bacillus* spp.: *An Examination of the transformation of Bacillus protoplasts by plasmids pUB110 and pHV33*, Current Microbiology, Vol 13 (1986), pp 191-195, the protoplast transformation in various bacilli was described. However the transformation in *B. coagulans* was reported as unsuccessful Electroporation is widely used for bacteria but requires species-specific (or even strain-specific) optimisation of the growth medium and electroporation buffer. Successful electroporation of *Bacillus* species often requires in vivo or in vitro methylation of plasmid DNA to prevent its restriction after transformation. WO 02/29030 discloses introduction of in vivo methylated plasmid in cells of a thermophilic *Bacillus* strain TN by electroporation. The plasmid used is based on the thermosensitive plasmid pUB110. However, we found that this plasmid did not yield transformed cells when used to transform moderately thermophilic *Bacillus* species that are facultative anaerobic and homolactic.

We have now found that genetic modification of moderately thermophilic *Bacillus* species that are facultative anaerobic and homolactic by genetic engineering is possible. Thus, the present invention for the first time shows the genetic engineering of moderately-thermophilic facultative-anaerobic homolactic *Bacillus* species by transformation. In addition to engineering said moderately thermophilic bacilli which are facultative anaerobic and homolactic for R-lactic acid production, the bacilli can also be genetically engineered for production of industrial compounds, including other organic acids than lactic acid, alcohol, enzymes, amino acids, and vitamins.

According to the invention, it is important that the moderately thermophilic *Bacillus* species is homolactic because this ensures that the newly introduced functionality will result in high yield production with a small amount of side products. Furthermore, the use of homolactic *Bacillus* species enables that only a few modifications have to be applied in order to obtain an industrially applicable micro-organism.

Moderately thermophilic *Bacillus* species are defined as bacteria that are capable of growing at temperatures between 30-65° C. Examples of moderately thermophilic facultative-anaerobic homolactic species are *Bacillus coagulans* and *Bacillus smithii*. Homolactic Bacilli can naturally produce S-lactate by homolactic fermentation. Which specific strains can produce lactic acid by homolactic fermentation can easily be determined by the person skilled in the art. The present invention also encompasses strains derived from moderately thermophilic facultative-anaerobic *Bacillus* species, wherein the homolactic phenotype is modified. Preferably a strain or derivative is chosen which is sporulation deficient.

As no literature was available on transformation of moderately thermophilic facultative-anaerobic homolactic Bacilli, the inventors needed to find a plasmid able to replicate in these Bacilli, needed to optimize the method for introduction of DNA into the cells and needed to find a suitable selectable marker for the defined group of *Bacillus* species, in order to be able to genetically engineer these Bacilli by transformation.

The inventors decided to use electroporation as the method to find out which plasmids could replicate in these Bacilli. Plasmids tested were pIL253 (See Simon, D., and A. Chopin, 1988: *Construction of a vector plasmid family and its use for molecular cloning in Streptococcus lactis*, Biochimie 70:559-566), pMV158 (See Burdett, V., 1980: *Identification of tetracycline resistant R-plasmids in Streptococcus agalactiae (group B)*, Antimicrob. Agents Chemother, 18: 753-766.), pHP13 (See Haima, P., S. Bron, G. Venema, 1987: *The effect of restriction on shotgun cloning and plasmid stability in Bacillus subtilis Marburg*. Mol. Gen. Genet. 209:335-342.), pUB110 (See Keggins, K. M., P. S. Lovett, E. J. Duvall, 1978: *Molecular cloning of genetically active fragments of Bacillus DNA in Bacillus subtilis and properties of the vector plasmid pUB110*, Proc. Natl. Acad. Sci. USA 75:1423-1427), pAMS100 (See Kiewiet, R., J. Kok, J. F. M. L. Seegers, G. Venema, S. Bron, 1993: *The mode of replication is a major factor in segregational plasmid instability in Lactococcus lactis*. Appl. Environ. Microbiol. 59:358-364), pWCFS105 (See Van Kranenburg, R., N. Golic, R. Bongers, R. J. Leer, W. M. de Vos, R. J. Siezen, M. Kleerebezem, 2005: *Functional anyalysis of three plasmids from Lactobacillus plantarum*, Appl. Environ. Microbiol. 71: 1223-1230), pNZ280 (See Platteeuw, C., F. Michiels, H. Joos, J. Seurinck, and W. M. de Vos, 1995: *Characterization and heterologous expression of the tetL gene and identification of iso-ISS1 elements from Enterococcus faecalis plasmid pJH1*, Gene 160: 89-93.), pNZ124 (See Platteeuw, C., G. Simons, and W. M. de Vos. 1994: *Use of the Escherichia coli β-glucuronidase (gusA) gene as a reporter gene for analyzing promoters in lactic acid bacteria*, Appl. Environ. Microbiol. 60:587-593), and pNW33n (See Zeigler, D. R. 2001: *The genus Geobacillus; introduction and strain catalog*, 7th ed., vol. 3. *Bacillus* Genetic Stock Center. After various trials, it was found that the latter three plasmids could replicate and yielded transformants.

Once a plasmid was identified that could replicate in these Bacilli, other process parameters relating to the transformation protocol could conveniently be optimized. In addition, other methods for the introduction of DNA, like natural transformation or conjugation, could be tested for their feasibility.

Tests with antibiotic resistance markers demonstrated that at least chloramphenicol resistance, tetracycline resistance and kanamycin resistance could be used. Care should be taken to avoid too low concentrations, since these could give rise to spontaneous antibiotic resistant colonies. Introduction of the erythromycin resistance gene from pIL253 cloned in pNZ124 or pNW33n yielded no transformants.

Thus, in a first aspect, the present invention discloses a method for genetic modification of moderately thermophilic *Bacillus* species that are facultative anaerobic and homolactic by means of genetic engineering. The method comprises the steps of:
introducing DNA cloned in a thermosensitive plasmid system containing a pSH71 replicon or a homologue thereof into cells of a moderately thermophilic *Bacillus* species that is facultative anaerobic and homolactic;
culturing the cells on a selective medium at a permissive temperature for plasmid replication to select transformed cells capable of growing on said selective medium at said permissive temperature;
culturing said transformed cells on a selective medium at a non-permissive temperature for plasmid replication to select transformed cells capable of growing on said selective medium at said non-permissive temperature.

The culturing of the cells at the permissive temperature on a selective medium allows for selection of transformants, i.e. cells that have taken up the transforming DNA. Preferably, transformed colonies are isolated prior to culturing the transformed cells at a non-permissive temperature, to allow checking the integrity of the transforming DNA. Cells of one or a few individual colonies are then cultured at a non-permissive temperature, to allow the selection of integrants.

According the invention, a DNA of interest is cloned in a thermosensitive plasmid system containing a pSH71 replicon (GenBank Accession Number A09338) or a homologue thereof. A pSH71 replicon is a replicon providing a thermosensitive replication functionality.

A thermosensitive replication functionality provides replication of a plasmid containing the replicon at a permissive temperature and lack of replication of said plasmid at a non-permissive temperature. This thermosensitive replication functionality of the pSH71 replicon is provided by an origin of replication and a replication protein (RepA) that is encoded by the replicon.

In the context of this invention, a "pSH71 replicon or a homologue thereof" is defined as a DNA comprising a DNA sequence encoding a polypeptide having a thermosensitive replication functionality (the RepA protein) and having an amino acid sequence of SEQ ID NO: 1 or an amino acid sequence that is 80% identical to SEQ ID NO:1, preferably 90% identical, more preferably 95, 96%, 97%, 98%, 99% identical. The pSH71 replicon or a homologue thereof further comprises an origin of replication where the RepA protein as defined above is capable to act upon. An example of a homologue of the pSH71 replicon is pWV01 (GenBank Accession Number X56954). The pSH71 replicon or a homologue thereof may further comprise a regulatory protein (RepC).

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands.

When chromosomal integration of the transforming DNA is intended, the availability of an integration plasmid with a conditional replicon is desirable. Such a plasmid can be introduced under permissive conditions after which the growth conditions can be changed (e.g. by a shift to a non-permissive temperature) making the plasmid non-replicating and allowing for selection for chromosomal integration events caused by homologous or non-homologous recombination. As a conditional cloning vector, a thermosensitive replicon can be used such as pSH71 present in pNZ124, or plasmids essentially identical (homologous) thereto or a derivative thereof having retained the plasmid's thermosensitive properties. Permissive temperatures for this replicon in moderately thermophilic *Bacillus* species that are facultative anaerobic and homolactic are preferably between 37 and 50° C. Non-permissive temperatures are preferably above 50° C. Permissive and non-permissive temperatures may not only depend on the replicon, but also on the host *Bacillus* species. The latter is a known phenomenom from the prior art, exemplified by pG+host plasmids for which 37° C. is a permissive temperature in *Lactobacillus delbrueckii* but a non-permissive temperature for *Lactococcus lactis* (See U.S. Pat. No. 5,919,678).

Conditional cloning vectors can also be obtained as thermosensitive derivatives of pNW33n or other plasmids able to replicate in moderately thermophilic *Bacillus* species that are facultative anaerobic and homolactic.

A DNA of interest cloned in a thermosensitive plasmid system containing a pSH71 replicon or a homologue thereof is introduced into cells of moderately thermophilic *Bacillus* species that are facultative anaerobic and homolactic by:

A. protoplast transformation or protoplast fusion,
B. electroporation,
C. biolistic transformation
D. conjugation, or
E. transformation of natural competent cells.

Transformation of these *Bacillus* species by electroporation can be achieved by a high-voltage discharge through a suspension containing a moderately thermophilic *Bacillus* species that is facultative anaerobic and homolactic and a suitable transforming DNA comprising the desired functionality and/or DNA sequences homologous to genomic sequences of the specific Bacilli.

Transformation of these *Bacillus* species by conjugation can be achieved by contacting (a population of) the moderately thermophilic *Bacillus* species that is facultative anaerobic and homolactic with (population of) a donor cell containing self-transmissible or mobilizable plasmid having the desired functionality. Self-transmissible plasmids encode all the functions they need to move among cells, and sometimes they also aid in the transfer of chromosomal DNA and mobilizable plasmids. Mobilizable plasmids do not encode all of the proteins required for transfer and consequently need these functions to be provided by the donor genome (chromosome or plasmid-encoded). Mobilizable plasmids at least contain an origin of transfer (oriT) region. Any donor cell which can be co-cultured with the moderately thermophilic *Bacillus* to be modified is in principle suitable to serve as a donor cell. Examples of suitable donor cells are those of *Bacillus* species, including *B. alkalophilus, B. amyloliquefaciens, B. brevis, B. cereus, B. circulans, B. coagulans, B. lautus, B. lentus, B. licheniformis, B. megaterium, B. smithii, B. subtilis, B. thermoamylovorans, B. thuringiensis, Geobacillus stearothermophilus, E. coli, Enterococcus faecalis, Lactobacillus* species, including *L. acidophilus, L. amylophilus, L. amylovorus, L. casei, L. coryniformis, L. crispatus, L. curvatus, L. delbrueckii, L. gasseri, L. helveticus, L. johnsonli, L. plantarum, L. reuteri, L. rhamnosus, L. sakei, L. sanfriscensis, Streptococcus* species, including *S. agalactiae, S. mutans, S. oralis, S. pneumoniae, S. salivarius, S. sobrinus*, and *S. thermophilus*. Suitable self-transmissible plasmids include pRK24, pLS20, pAMβ1, or a plasmid essentially identical thereto or a derivative hereof having retained the plasmid's self-transmissible capability. Suitable mobilizable plasmids include pAT18, pAT28, pJS28, or a plasmid essentially identical thereto or a derivative hereof having retained the plasmid's mobilizing capability.

The inventors further managed to develop a natural transformation protocol for these *Bacillus* species. This required determining the right medium composition for growth, starvation, and transformation, the right timing for developing and harvesting competent cells, and the right transformation procedure. While natural transformation is not known to be wide-spread among *Bacillus* species the inventors discovered that moderately thermophilic bacilli that are facultative anaerobic and homolactic can be made naturally competent.

For electroporation and protoplast transformation, the source of the transforming DNA may influence the transformation outcome. The source of the DNA to be transformed (isolated from either *Lactococcus lactis* MG 1363, *Escherichia coli* DH5α, *E. coli* JM109, or *E. coli* JM110) did not affect transformation efficiencies in the present *Bacillus* species, indicating that the methylation state of the DNA is not important. This is in contrast to other *Bacillus* species (see e.g. WO 02/29030).

In a preferred embodiment of the invention, the transforming DNA for introduction into *Bacillus* is isolated from *Lactococcus lactis*. More preferably, cloning steps to construct the transforming DNA are also performed in *Lactococcus lactis*. This, because cloning in *E. coli* often appeared to result in deletions and/or rearrangements in the cloned DNA.

With the present invention, methods for transformation by preferably induction of natural competence, transformation of electrocompetent cells, and conjugation are provided, the use of a a thermosensitive plasmid is demonstrated, and application of these elements for the production of genetically engineered moderately thermophilic *Bacillus* species that are facultative anaerobic and homolactic, for instance for the production of R-lactate, is demonstrated.

The transforming DNA contains a pSH71 replicon or a homologue thereof and a DNA of interest capable of providing a desired functionality to the *Bacillus* cells.

Chromosomal modification is the preferred modification of moderately thermophilic *Bacillus* species that are facultative anaerobic and homolactic, since chromosomal modification will ensure a stable distribution of said functionality over the progeny cells. Introduction of a desired functionality in the chromosome can be done with non-homologous as well as with homologous recombination. Homologous recombination is preferred, as it opens the opportunity to introduce, to remove or to simultaneously introduce and remove a functionality.

In the context of the invention, a functionality may be a gene encoding a desired polypeptide to be produced by the cell and/or a gene encoding a polypeptide involved in production of a primary or secondary metabolite by the cell and/or a DNA sequence enabling deletion of a DNA sequence from the chromosome of the cell.

Genes encoding polypeptides are provided with regulatory sequences functional in the cell, for instance a promoter sequence. The regulatory sequences may be sequences that are natively associated with the coding sequence, or may be heterologous thereto.

A gene encoding a polypeptide may be fused to any regulatory or promoter sequence functioning in the *Bacillus* species of choice. Suitable promoter sequences include promoters obtainable from the *Bacillus* species of choice, hybrid promoters derived from different native *Bacillus* promoters and artificial promoters. A preferred promoter is the promoter of a *Bacillus* gene to be inactivated by homologous recombination. Especially preferred is the IdhL promoter from *Bacillus coagulans*. or the promoter of the amylase gene as disclosed in U.S. Pat. No. 5,171,673.

To enable selection of transformed *Bacillus* cells from the majority of untransformed cells, a selection marker is part of the transforming DNA. The selection marker may be present on the same DNA fragment or plasmid as the functionality of interest or on a separate DNA fragment or plasmid. A preferred selection marker is the cat gene coding for chloramphenicol acetyltransferase from pMH3.

Desired functionalities that can be introduced are R-lactic acid production as described below, and other functionalities that provide the production of compounds that are metabolizable from pyruvate. Examples of these compounds are pyruvate, acetolactate, diacetyl, acetoin, 2,3-butanediol, 1,2-propanediol, acetate, formate, acetaldehyde, ethanol, L-alanine, oxaloacetate, S-malate, succinate, fumarate, 2-oxoglutarate, oxalosuccinate, isocitrate, citrate, glyoxylate.

When homologous recombination is intended, the transforming DNA further contains a DNA sequence that is homologous to a genomic target sequence of the specific *Bacillus* to be engineered. The skilled person will understand that no 100% identity is required to obtain homologous recombination. A percentage identity of about 90% will also suffice. Generally, the DNA sequence of interest to be inserted in the chromosome by homologous recombination is flanked by homologous sequences with a sufficient length to enable homologous recombination. Such a length may be at least about 200 bp, for instance between about 200 and about 1500 bp, preferably between about 200 and about 1000 bp.

The present invention is directed to the modification by means of genetic engineering of moderately thermophilic *Bacillus* species that are facultative anaerobic and homolactic wherein a desired functionality is introduced, preferably by homologous recombination.

The present invention is also directed to the modification by means of genetic engineering of moderately thermophilic *Bacillus* species that are facultative anaerobic and homolactic wherein an undesired functionality is removed by homologous recombination.

The invention is further directed to the modification by means of genetic engineering of moderately thermophilic *Bacillus* species that are facultative anaerobic and homolactic wherein a desired functionality is introduced in the chromosome and at the same time an undesired functionality is removed by homologous recombination.

The genetically engineered moderately thermophilic *Bacillus* strains that are facultative anaerobic and homolactic or derivatives of a parent strain that is homolactic, that are obtainable by said modification by means of genetic engineering form a further aspect of this invention. The modification by means of genetic engineered includes introduction of a functionality in, removal of a functionality from or simultaneous introduction of a functionality in and removal of a functionality from the bacterial chromosome.

In a preferred embodiment, the modification by means of genetic engineered occurs by homologous recombination.

In one preferred embodiment, the genetically engineered derivative of a moderately thermophilic *Bacillus* species that is facultative anaerobic and homolactic is a strain wherein the conversion of pyruvate to lactate is blocked and pyruvate accumulates, or wherein additional modifications are applied to redirect pyruvate towards production of other products including acetolactate, diacetyl, acetoin, 2,3-butanediol, 1,2-propanediol, acetate, formate, acetaldehyde, ethanol, L-alanine, oxaloacetate, S-malate, succinate, fumarate, 2-oxoglutarate, oxalosuccinate, isocitrate, citrate, glyoxylate.

In another preferred embodiment, the genetically engineered derivative of a moderately thermophilic *Bacillus* species that is facultative anaerobic and homolactic is a strain wherein the IdhL gene coding for S-lactate dehydrogenase activity is removed by homologous recombination.

In another preferred embodiment, the genetically engineered derivative of a moderately thermophilic *Bacillus* species that is facultative anaerobic and homolactic is a strain wherein the IdhL gene coding for S-lactate dehydrogenase activity is replaced with a gene coding for an NADH-dependent 2-hydroxyacid dehydrogenase having R-lactate dehydrogenase activity by homologous recombination.

In these embodiment, the construct that is used for homologous recombination contains a defective IdhL gene that does not encode a functional S-lactate dehydrogenase enzyme. A defective IdhL gene can be provided by a construct wherein part or all of the IdhL coding sequence is deleted.

A defective IdhL gene may be created by replacing part or all of the IdhL gene with another gene, for instance a gene encoding a selection marker or a gene of interest. Preferably, the IdhL gene coding for S-lactate dehydrogenase activity is replaced by a construct containing a gene coding for an NADH-dependent 2-hydroxyacid dehydrogenase having R-lactate dehydrogenase activity, including enzymes with EC number EC 1.1.1.28.

Suitable genes coding for R-lactate dehydrogenase activity are those genes that are able to complement an *E. coli* IdhA mutant, such as *E. coli* FMJ144 as described by Bernard et al. (See Bernard, N., T. Ferrain, D. Garmyn, P. Hols, and J. Delcour, 1991: *Cloning of the D-lactate dehydrogenase gene from Lactobacillus delbrueckii subsp. bulgaricus by complementation in Escherichia coli*. FEBS Lett. 290:61-64). A suitable IdhA gene coding for R-lactate dehydrogenase activity for instance is the IdhA gene from *Lactobacillus delbrueckii* subsp. *bulgaricus* (see also Bernard et al.) or the hdhD gene from the same species (Bernard, N., K. Johnsen, T. Ferain, D. Garmyn, P. Hols, J. J. Holbrook, and J. Delcour. 1994. *NAD$^+$-dependent D-2-hydroxvisocaproate dehydrogenase of Lactobacillus delbrueckii subsp. bulgaricus*. Eur. J. Biochem. 224:439-446). The amino acid sequence of the R-lactate dehydrogenase encoded by the IdhA gene is depicted in SEQ ID NO: 2. It appears that polypeptides encoded by genes capable of the complementation of the above *E. coli* mutant substantially differ in amino acid sequence. A percentage identity as low as 30% with the amino acid sequence of SEQ ID NO: 2 is feasible. The IdhA and the hdhD genes appear to encode proteins with a degree of identity of about 50%.

Suitable genes coding for R-lactate dehydrogenase activity are those genes that encode an amino acid sequence of SEQ ID NO:2 or homologous genes that encode an amino acid sequence that displays a degree of identity of at least 30%, more preferably at least 40%, even more preferably at least 50%, 60%, 70%, 80%, 90%, to the amino acid sequence of SEQ ID NO: 2 and that are able to complement an *E. coli* IdhA$^-$ mutant, such as *E. coli* FMJ144. Such homologous sequences may encompass polymorphisms that may exist in cells from different populations or within a population due to natural allelic or intra-strain variation. A homologue may further be derived from a *Bacillus* species other than the species where the specified DNA or amino acid sequence originates from, or may be artificially designed and synthesized.

In addition to introducing desired functionalities, genetic engineering can be used to optimize the industrial fermentation, e.g. to enable the fermentation of cheap substrates like lignocellulose-derived sugars including xylose and arabinose and/or to remove undesired functionalities.

In a further aspect, the present invention provides a process for the production of a compound of interest comprising culturing the genetically engineered strain of the previous aspect under conditions conducive to production of said compound.

DESCRIPTION OF THE FIGURES

FIG. 3 shows the nucleotide sequence (SEQ ID NO: 16) of a synthetic B. coagulans ATTC 23498 amylase promoter region based on the sequence disclosed in U.S. Pat. No. 5,171,673. Bg/II (AGATC), BamHI (GGATCC), and NcoI (CCATGG) cloning sites are underlined. The NcoI site allows translational fusion to the amylase promoter. The ATG start codon of the amylase gene is depicted boldface.

Figure 1:
FIG. 1 shows restriction analyses of pNW33N isolated from three E. coli isolates that were transformed with plasmid material isolated from three transformed B. coagulans DSM 1 isolates. Lanes 1, 4, and 7. pNW33N digested with EcoRI; 4217-bp fragment. Lanes 2, 5, and 8. pNW33N digested with EcoRI-StuI; 333-bp and 3884-bp fragments. Lanes 3 and 6. Kb DNA ladder (Stratagene) 250 bp, 500 bp, 750 bp, 1.0 kb, 1.5 kb, 2.0 kb, 3.0 kb, 4.0 kb, 5.0 kb, 6.0 kb, 7.0 kb, 8.0 kb, 9.0 kb, 10.0 kb, and 12.0 kb.

The present invention is further illustrated by means of the following non-limitative Examples.

EXAMPLES

Materials and Methods
Plasmids and Strains

Plasmid pNZ124 (Platteeuw, C., G. Simons, and W. M. de Vos. 1994. Use of the Escherichia coli β-glucuronidase (gusA) gene as a reporter gene for analyzing promoters in lactic acid bacteria. Appl. Environ. Microbiol. 60:587-593) was obtained from NIZO food research. It is based on the cloning vector pNZ12 disclosed in EP 0228726 B1. Plasmid pNW33N (Zeigler, D. R. 2001: The genus Geobacillus; introduction and strain catalog, 7th ed., vol. 3. Bacillus Genetic Stock Center.) was obtained from the Bacillus Genetic Stock Center, Ohio State University, Columbus, Ohio, USA, and propagated in Escherichia coli DH5a (Invitrogen Life Technologies). The nucleotide sequence of pNW33N is available under GenBank accession number AY237122. Plasmid pATΔS28 containing the IncP plasmid RK2 origin of transfer (oriT) (Namy, O., M. Mock, A. Fouet, 1999: Co-existence of clpB and clpC in the Baciliceae. FEMS Microbiol. Lett. 173: 297-302) was obtained from Institute Pasteur.

B. coagulans DSM 1 was obtained from DSMZ, Braunschweig, Germany. Lactococcus lactis subsp. cremoris MG1363 was described by Gasson (M. J. Gasson. 1983: Plasmid complements of Streotococcus lactis NCDO 712 and other lactic streptococci after protoplast-induced curing. J. Bacteriol. 154:1-9).

Lactobacillus delbrueckii subsp. bulgaricus LMG 6901 was obtained from the BCCM/LMG bacteria collection, Gent, Belgium.

E. coli HB101 harbouring pRK24 was described by Trieu-Cuot, et al. (Trieu-Cuot, P., C. Carlier, P. Martin, and P. Courvalin, 1987: Plasmid transfer by coniuqation from Escherichia coli to Gram-positive bacteria. FEMS Microbiol. Lett. 48:289-294).

Culture Conditions

B. coagulans was routinely grown at 45° C. under aerobic conditions in BC-broth (BC for B. coagulans) containing 10 g/L yeast extract, 2 g/L di-ammoniumphosphate, 3.5 g/L di-ammoniumsulphate, 10 g/L Bis-Tris buffer (bis[2-hydroxymethyl]iminotris[hydroxymethyl]-methane), 3 mg/L $CaCl_2$, 5 mg/L $MgCl_2$. if appropriate the medium was supplemented with 50 g/L sucrose; pH was adjusted to 6.6-6.7 and medium was autoclaved (20 min 121° C.) before use. For plates the medium was supplemented with 10 g/L Gelrite and 1 g/L $MgCl_2$. Filter sterilised trace elements were added separately. Final concentrations were: 0.2 mg/L $CoCl_2.6H_2O$, 0.01 mg/L $CuCl_2.2H_2O$, 0.3 mg/L $H_3BO_3$, 0.03 mg/L $Na_2MoO_4.2H_2O$, 0.02 mg/L $NiSO_4.6H_2O$, 0.03 mg/L $MnCl_2.4H_2O$, 0.05 mg/L $ZnCl_2$. If appropriate, the media were supplemented with filter sterilised chloramphenicol at 7 mg/L. Competence medium (C-broth) contained 0.05 g/L yeast extract, 2 g/L di-ammoniumphosphate, 3.5 g/L di-ammoniumsulphate, 10 g/L glucose, 10 mg/L $CaCl_2$, 0.5 g/L KCl, 25 mg/L $MgCl_2$; pH was adjusted to 6.8 and medium was autoclaved (20 min 121° C.) before use. Filter sterilised trace elements and vitamins were added separately. Final concentrations were: 2.4 mg/L $CoCL_2$, 3.6 mg/L $FeCl_3$, 3 mg/L $MnCl_2$, 1.2 mg/L $ZnCl_2$, 0.024 mg/L biotine, 0.012 mg/L thiamine, 20 mg/L methionine. Transformation medium (T-broth) was C-broth with 0.025 g/L yeast extract instead of 0.05 g/L.

E. coli was routinely cultured in LB broth (Molecular Cloning, a laboratory manual. 3$^{rd}$ edition. J. Sambrook and D. W. Russell. 2001. Cold Spring Harbor Laboratory Press, New York) at 37° C. under aerobic conditions. When appropriate chloramphenicol and/or ampicillin were used at concentrations of 5 mg/L and 100 mg/L, respectively.

L. bulgaricus was routinely cultured in MRS Broth® (BD Biosciences) at 37° C. under anaerobic conditions.

L. lactis was routinely cultured in Ml 7 Broth® (BD Biosciences) supplemented with 0.5% glucose at 30° C. under anaerobic conditions. When appropriate chloramphenicol was used at a concentration of 5 mg/L.

DNA Manipulation Techniques

Standard DNA manipulation techniques were performed as described by Sambrook and Russell (J. Sambrook and D. W. Russell. 2001: Molecular Cloning, a laboratory manual. 3$^{rd}$ edition. Cold Spring Harbor Laboratory Press, New York).

Construction of pNZ124 and pNW33N derivatives was performed in L. lactis and E. coli, respectively.

Large-scale E. coli plasmid DNA isolation from 100 mL culture was performed using the Jetstar 2.0 Plasmid Maxiprep Kit® (Genomed) following the instructions of the manufacturer. Small-scale *E. coli* plasmid DNA isolation from 1 mL culture was performed using the Nucleospin Plasmid Quick Pure® (Macherey-Nagel) kit following the instructions of the manufacturer.

Large-scale *B. coagulans* plasmid DNA isolation was performed using equilibrium centrifugation in cesium chloride-ethidium bromide gradients. Two overnight cultures of 300 mL grown under aerobic conditions (170 rpm) at 45° C. were harvested by centrifugation. The cell pellets were pooled and resuspended in 7 mL of a buffer containing 2 mg/mL lysozyme, 30 mM Tris/HCl, pH 8.0, 3 mM $MgCl_2$, and 25% sucrose, and was incubated for 15 minutes on ice. Cells were lysed by addition of 16 mL of a solution containing 0.2 M NaOH and 1% SDS. After 5 min. incubation on ice the sample was neutralized by addition of 12 mL of 3M KAc and mixing. Precipitates were removed by centrifugation. The DNAs in the supernatants were precipitated by addition of 20 mL of isopropanol. The DNAs were pelleted by centrifugation, dried and dissolved in TE buffer containing 1.0 g/mL CsCl and 0.4 mg/mL ethidiumbromide. Chromosomal and plasmid DNAs were separated by cesiumchloride density gradients using a vertical rotor (Stepsaver 65 V13®; Sorvall) at 45000 rpm for 16 h. Plasmid DNA was collected and ethidium bromide was removed as described elsewhere (*Molecular Cloning, a laboratory manual. 3$^{rd}$ edition*. J. Sambrook and D. W. Russell. 2001. Cold Spring Harbor Laboratory Press, New York).

Small-scale *L. lactis* and *B. coagulans* plasmid DNA isolation from 10 mL culture was performed following a miniprep protocol for Gram-positive bacteria (*Rapid mini-prep isolation of high quality plasmid DNA from Lactococcus and Lactobacillus* spp. D. J. O'Sullivan and T. R. Klaenhammer. 1993. Appl. Environ. Microbiol. 59:2730-2733). *E. coli* competent cells were prepared using calcium chloride and transformed by heat shock as described by Sambrook and Russell (*Molecular Cloning, a laboratory manual. 3$^{rd}$ edition*. J. Sambrook and D. W. Russell. 2001. Cold Spring Harbor Laboratory Press, New York). *L. lactis* was transformed by electroporation as described by Holo and Nes (High-frequency transformation by electroporation of *Lactococcus lactis* subsp. cremoris grown with glycine in osmotically stabilized media. 1989. Holo, H., and I. F. Nes. Appl. Environ. Microbiol. 55:3119-3123).

PCR reactions for cloning purposes were performed with the high-fidelity Pwo polymerase (Roche) following the instructions of the manufacturer.

Colony-PCR analysis was used to demonstrate the presence of pNW33N in the chloramphenicol resistant colonies. PCR primers were designed for identification of the pNW33N replication gene repB with the sequences 5'-TCGCCTTCTTCTGTGTCATC-3' (SEQ ID NO: 3) and 5'-CTGGAGGAGAGCAATGAAAC-3' (SEQ ID NO: 4). Colonies were picked with tooth pick and a little cell material was transferred to a 0.5 mL PCR reaction tube. The cells were disrupted by 1 min incubation at 1000 W in a microwave oven. PCR reaction mixtures of 50 µL with rTaq polymerase (Amersham Biosciences) and 0.5 µg of each primer were prepared as recommended by the manufacturer and added to the reaction tubes with the disrupted cells. PCR reactions were performed in a RoboCycler® (Stratagene). 4 min of incubation at 94° C. was followed by 25 cycles of 30 sec at 94° C. for denaturation, 1 min at 58° C. for primer annealing, and 1 min at 72° C. for elongation. After the final cycle the reaction mixture was incubated at 72° C. for another 5 min.

Electroporation

Preparation of electrocompetent cells required determination of the proper culture conditions, time of harvest, and composition of wash and electroporation buffers. Although *B. coagulans* DSM 1 is able to grow on LB broth, the developed BC broth increased electroporation efficiencies. Glycine was added to weaken the cell wall, and the concentrations were optimized. Glycine concentrations were between 0.5 and 2.0% and preferably between 1.0 and 1.5%. Cells were harvested at early to mid-log phase for optimal results. The electroporation buffer had a pH between 4.3 and 6.0 and preferably between 4.3 and 5.0. The optimal electroporation settings (voltage, resistance, capacitance) also needed to be determined. Voltage preferably was between 1.0 and 2.5 kV, and more preferably between 1.25 and 2.0 kV. Resistance was preferably between 100 and 800Ω, and more preferably between 200 and 600Ω. Recovery before plating on a selective medium is important and was at least 2 hours and preferably 3 hours.

Electrocompetent cells of *B. coagulans* were prepared as follows. An overnight culture was used to inoculate (5% volume/volume) 50 mL of medium supplemented with 1% glycine (resulting in a turbidity at 600 nm of approximately 0.13-0.14). After 2.5 hrs of aerobic incubation at 45° C. cells were harvested by centrifugation. Cell pellets were washed twice with 50 mL and 25 mL, respectively, of ice-cold electroporation buffer (5 mM $KH_2PO_4$, 0.4 M sorbitol, 10% glycerol, 4 mM $MgCl_2$ adjusted to pH 4.5), and resuspended in 1 mL of ice-cold electroporation buffer. For electroporation, 100 µL of the cell suspension was mixed with 1 µg plasmid DNA and transferred to a 0.2 cm electroporation cuvet (Bio-Rad®) that was precooled on ice. The sample was subjected to a 1.6 kV pulse at 200Ω and 25 µF using a Gene Pulser and a Pulse Controller apparatus (Bio-Rad®). Immediately after electroporation 1 mL of medium was added and the cells were incubated for 3 hours at 45° C. in a Thermomixer® (Eppendorf) at 900 rpm, after which they were plated on plates supplemented with chloramphenicol. The plates were incubated at 45° C. for 1 to 2 days under aerobic conditions.

Conjugation

Filter matings were used for conjugal transfer of recombinant plasmids from *E. coli* to *B. coagulans*. Logarithmic growing cells of donor (2 mL) and recipient (2 mL) were pooled and using a syringe harvested on a 0.45 µm cellulose acetate filter (Schleiger & Schuell) sterilized in a plastic filter holder (Schleiger & Schuell). Cells were washed with 10 mL of BC-broth and the filters were dried by forcing air through the filter. Filters were placed on the surface of BC-plates without antibiotics and incubated overnight at 45° C. After the mating the cells were resuspended from the filter in BC-broth and dilution series were plated on BC-plates containing 7 mg/L chloramphenicol and incubated at 55° C. aerobically for 1-2 days.

Enzyme Analyses

Enzyme overproduction in *B. coagulans* using the *B. coagulans* promoter was determined in exponentially growing cultures. Cells were harvested by centrifugation. Cell-free extracts were prepared using a FastPrep FP120® apparatus (Qbiogene) in two runs of 30 sec at speed 4. Cells were cooled on ice for 1 min between the runs. Protein content was determined by the method of Bradford (Bio-Rad) using Bovine Serum Albumine as a standard. SDS-PAGE (12.5%) was performed as described by Sambrook and Russell (*Molecular Cloning, a laboratory manual. 3$^{rd}$ edition*. J. Sambrook and D. W. Russell. 2001. Cold Spring Harbor Laboratory Press, New York) using the Protean II electrophoresis system (Bio-Rad).

R-lactate dehydrogenase-specific activities were determined spectrophotometrically at 340 nm and carried out at 50° C., using 1 ml of an assay mix containing 0.3 M glycylglycine buffer pH10, 0.25% (v/v) Triton X-100, 5 mM NAD, and 1% R-lactate. The reaction was started by the addition of 40 or 50 μL of cell-free extract. Specific activities were expressed as $\Delta A \cdot min^{-1} \cdot mg^{-1}$ where $\Delta A$ is the increase in absorbance at 340 nm for 1 cm path length and mg the amount of protein.

Fermentations

Batch fermentations were performed in a bioreactor (7 L Applikon®) with 4 L of BC broth without Bis-Tris buffer and supplemented with 30 g/L glucose. An overnight aerobic culture (40 mL) grown at 50° C. and inoculated from glycerolstock was transferred to 360 mL fresh BC broth and incubated for another 4-5 hrs. This 400 mL was used to inoculate the bioreactor. The pH maintenance was achieved by the automatic addition of a lime solution at 20% (w/v). The fermentation was performed at 54° C., pH 6.5 and agitation speed of 250-300 rpm. The temperature control was performed with a water bath (Lauda) while the pH reading/control was performed by ADI 1020 Bio-Processor (Applikon®). All the data (pH and base consumption) were processed by online data acquisition (Applikon FM V5.0®). Samples were withdrawn before inoculation and at the end of fermentation for measurement of R- and S-lactic acid, and possible by-products. Samples were centrifuged and remaining debris was removed by filtration using a Millex GP 0.22 μm Filter® (Millipore). Filtrate was stored at −21° C. until further analysis.

Organic acids (lactic acid, acetic acid, formic acid, succinic acid) were measured using a derivatisation and GLC. R- and S-lactates were methylated to methyl-lactate and measured by headspace analysis on a chiral column.

Results

Example 1

Transformation of B. Coagulans with Plasmid pNW33N Using Natural Competent Cells 1) Preparation of Competent Cells of B. Coagulans DSM 1

In three independent experiments the following procedures were used. Bacillus coagulans DSM 1 was cultured overnight at 45° C. in 5 ml BC-broth under aerobic conditions. This culture was used to inoculate 25 ml of prewarmed C-broth resulting in a turbidity at 600 nm of 0.15. The fresh culture was incubated aerobically at 45° C. until a turbidity at 600 nm between 0.9-1.2 was reached (Table 1).

2) Transformation of B. Coagulans DSM 1 with pNW33N

A 0.5 mL portion of the competent cells was pelleted and the pellet was resuspended in 0.1 mL of T-broth and mixed with 5 μg of pNW33N plasmid DNA. After 1.5 h incubation at 45° C. in a Thermomixer (Eppendorf) at 900 rpm, 0.3 mL of prewarmed BC broth was added and the incubation was continued for 2 h, after which the cells were plated on BC plates supplemented with 7 mg/L chloramphenicol. The plates were incubated aerobically at 45° C. After 3 days of incubation colonies had appeared (Table 1).

TABLE 1

| Natural transformation of B. coagulans DSM 1 | |
|---|---|
| Turbidity at 600 nm | Number of colonies |
| 0.92 | 24 |
| 0.97 | 3 |
| 1.16 | 2 |

3) Plasmid Isolation from B. Coagulans DSM 1

The colonies were striped to fresh BC plates supplemented with 7 mg/L chloramphenicol for overnight incubation at 45° C. Colony PCR was used to detect the presence of the repB gene from plasmid pNW33N. All PCR reactions yielded a product of the expected size. One colony from each experiment was transferred to BC-broth for O/N incubation and miniprep plasmid isolation. Although no plasmid DNA could be visualized by agarose gel electrophoresis, transformation of E. coli DH5α with this miniprep DNA resulted in transformants from which pNW33N could be retrieved. Plasmid DNA was digested with EcoRI-StuI to confirm the integrity of pNW33N. The restriction patterns were as expected (FIG. 1) demonstrating that plasmid pNW33N was transformed to B. coagulans DSM 1.

Example 2

Transformation of B. Coagulans with Plasmid pNW33N Using Electroporation

B. coagulans DSM 1 was routinely transformed with 1 μg plasmid pNW33N by electroporation. Typically, after 1 day of incubation at 45° C. more than 20 colonies appeared on chloramphenicol-containing plates. In one experiment 15 colonies were transferred to fresh chloramphenicol-containing plates after 2 days of incubation. After 24 h of incubation at 45° C. transformation was confirmed by colony-PCR analysis using repB-specific primers. PCR products of the expected size were obtained for all transformants tested, demonstrating that the repB gene of pNW33N was present. B. coagulans DSM 1 was used as negative control and yielded no PCR products. Plasmid DNA of a single transformant was isolated from a cesium-chloride gradient. Plasmid DNA was digested with EcoRI and with EcoRI-StuI to confirm the integrity of pNW33N. The restriction patterns were as expected (333-bp and 3884-bp fragments) demonstrating that plasmid pNW33N was transformed to B. coagulans DSM 1.

Example 3

Transformation of B. Coagulans with Plasmid pNW33N Using Conjugation

1) Construction of pNW33N-Derivative Containing an Origin of Transfer.

Figure 2:
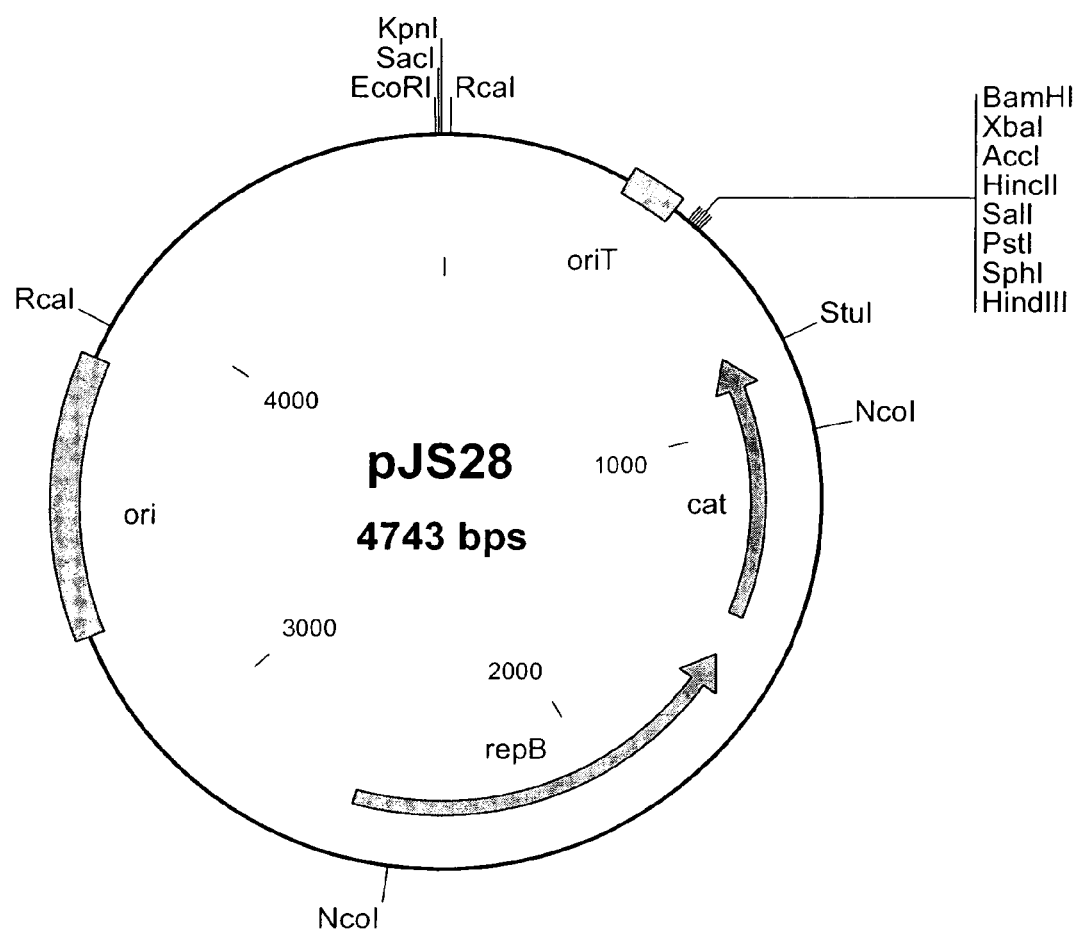
FIG. 2 shows a plasmid map of pJS28. The replication gene (repB) and the chloramphenicol resistance gene (cat) are depicted by arrows. The IncP plasmid RK2 origin of transfer (oriT) and the E. coli origin of replication (ori) are depicted as boxed regions.

The origin of transfer (oriT) of the IncP plasmid RK2 was cloned into pNW33N. This allows effective comobilization by any self-transferable IncP plasmid co-resident in E. coli donors (Plasmid transfer by conjugation from Escherichia coli to Gram-positive bacteria. Trieu-Cuot, P., Carlier, C., Martin, P., and Courvalin, P. 1987. FEMS Microbiol. Lett. 48:289-294). The RK2 oriT region was cloned as a blunted 0.5-kb AccI-AvaII fragment derived from pATΔS28 in pNW33N digested with SmaI. The resulting plasmid, pJS28 (FIG. 2), was transformed to E. coli HB101 harbouring pRK24. This strain was used as donor in plate matings with B. coagulans DSM 1.

2) Conjugal Transfer of pJS28 from E. Coli to B. Coagulans.

An overnight culture of E. coli harbouring pJS28 and pRK24 grown aerobically at 37° C. in LB containing ampicillin and chloramphenicol was transferred ⅟50 to fresh LB broth with antibiotics and cultured to a turbidity at 600 nm of 0.56. An overnight culture of B. coagulans DSM 1 grown aerobically at 45° C. in BC broth was transferred ⅟50 to fresh BC broth and cultured to a turbidity at 600 nm of 0.52. Equal volumes (2 mL) of E. coli and B. coagulans were harvested on a 0.45 μm filter. The filter containing the cells was transferred to BC plates without antibiotics and incubated overnight at 45° C. The cells were removed from the filter and dilution series were plated on BC plates and incubated at 55° C. aerobically. After 1-2 days colonies appeared. The presence of pJS28 was confirmed by plasmid DNA isolation and the integrity was confirmed by digestion with NcoI yielding the expected digestion pattern (1444-bp and 3299-bp fragments). The efficiency of conjugation was approximately 9.3 $10^{-7}$ per recipient.

Example 4

Construction of a *B. Coagulans*-Derived Expression System

1) Construction of *B. Coagulans* Expression System

Figure 4:
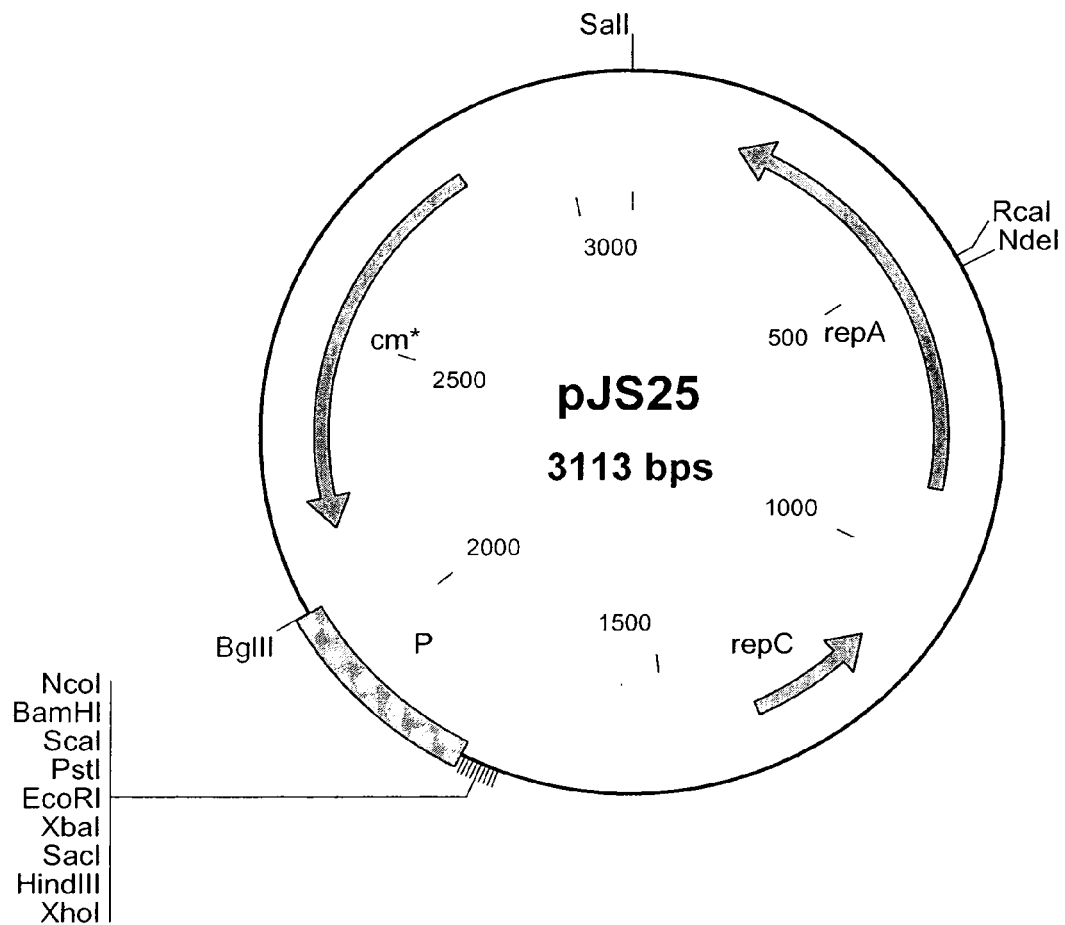
FIG. 4 shows a plasmid map of pJS25. Replication genes (repA and repC), the chloramphenicol resistance gene without NcoI site (cm*) are indicated by arrows. The B. coagulans promoter region (P) is depicted as boxed region.

A *B. coagulans* ATCC 23498 nucleotide sequence fragment (disclosed in U.S. Pat. No. 5,171,673) having promoter activity was produced as a synthetic DNA fragment (FIG. 3) and cloned as BglII-BamHI fragment into pMH3 digested with the same enzymes. The resulting cloning vector, pJS25 (FIG. 3), allows translational fusion to this promoter by the use of an NcoI site overlapping the start codon. To enable the use of this NcoI site, first plasmid pMH3 was constructed from plasmid pNZ124 by removing the NcoI site from the cat gene using a megaprimer. Primers with the sequences 5'-CTATTATTCCGTGGACTTC-3' (SEQ ID NO: 5) and CAGCTGAGATCTTGGAG-3' (SEQ ID NO: 6) were used to generate the megaprimer, which was used in a second PCR reaction in combination with a primer having the sequence 5'-GACGAAAGTCGACGGCAATAGTTAC-3' (SEQ ID NO: 7). The resulting PCR product encompassed the complete cat gene and was digested with BglII-SalI to replace the pNZ124 cat gene generating plasmid pMH3. Plasmid pJS25 (FIG. 4) can be used in various mesophilic Gram-positive organisms including *Bacillus subtilis, Lactobacillus casei, Lactobacillus plantarum, Lactococcus lactis,* and *Leuconostoc lactis,* and the Gram-negative organism *Escherichia coli* (*Use of the Escherichia coli β-glucuronidase (gusA) gene as a reporter gene for analyzing promoters in lactic acid bacteria*. C. Platteeuw, G. Simons, and W. M. de Vos. 1994. Appl. Environ. Microbiol. 60:587-593).

2) Construction of ldhA Overexpression System

Figure 5:
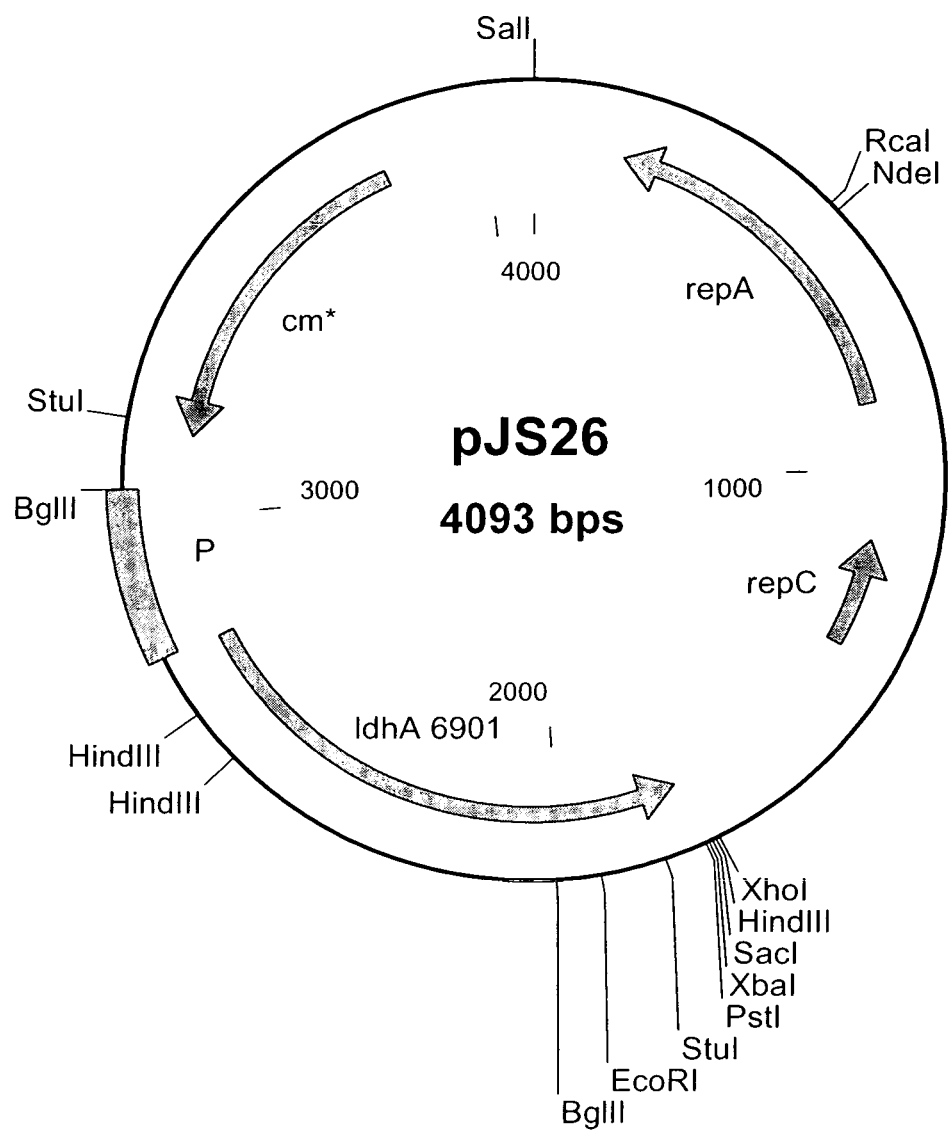
FIG. 5 shows a plasmid map of pJS26. Replication genes (repA and repC), the chloramphenicol resistance gene without NcoI site (cm*), and the LMG 6901 IdhA gene (IdhA 6901) are indicated by arrows. The B. coagulans promoter region (P) is boxed.
Figure 6:
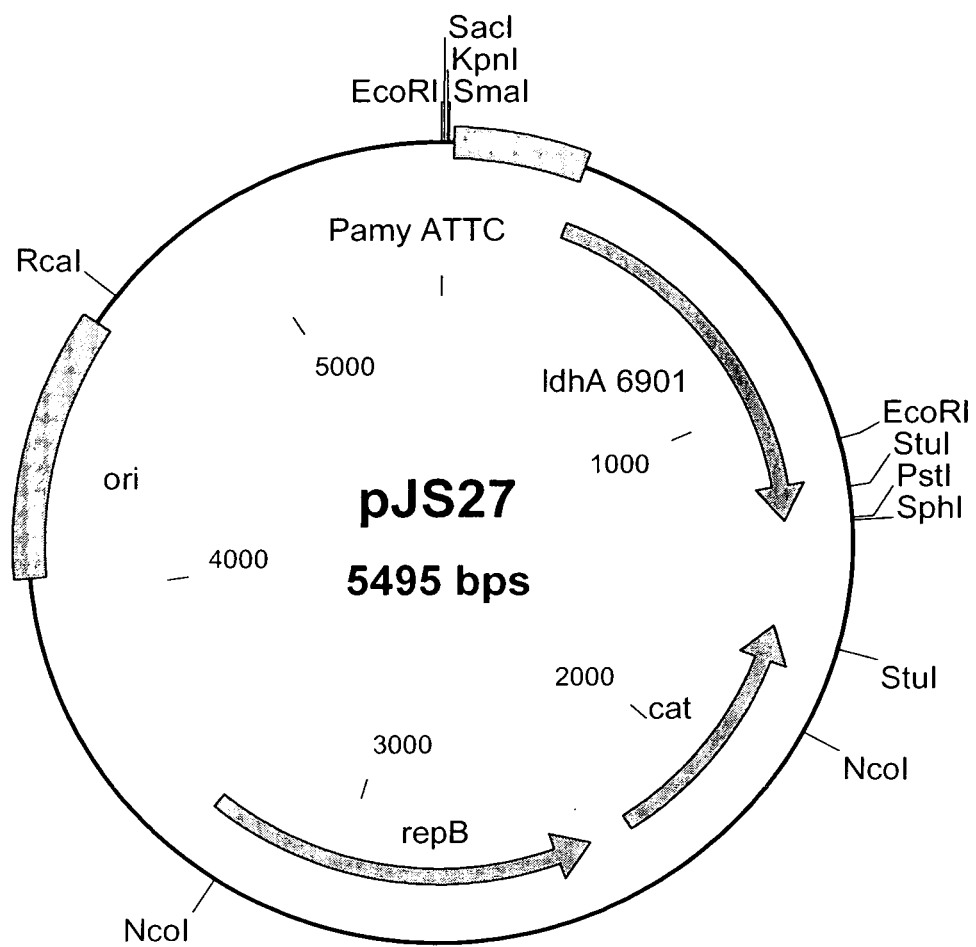
FIG. 6 shows a plasmid map of pJS27. The replication gene (repB), the chloramphenicol resistance gene (cat), and the L. bulgaricus LMG 6901 IdhA gene (IdhA 6901) are depicted by arrows. The B. coagulans promoter region (P) and the E. coli origin of replication (ori) are depicted as boxed regions.

The *L. bulgaricus* LMG 6901 ldhA gene encoding an R-lactate dehydrogenase and published by Bernard et al. (*Cloning of the D-lactate dehydrogenase gene from Lactobacillus delbrueckii subsp. bulgaricus by complementation in Escherichia coli.* 1991. Bernard, N., T. Ferrain, D. Garmyn, P. Hols, and J. Delcour. FEBS Lett. 290:61-64) was generated by PCR using primers with the sequences 5'-GACAATTCAT-GACTAAAATTTTTGC-3' (SEQ ID NO: 8) and 5'GGATTTCTCTAGACTGCAGTTAGCCAACCTTAA-3' (SEQ ID NO: 9) The PCR product was cloned as a blunt-XbaI fragment into pUC18 digested with XbaI-SmaI and its integrity was confirmed by nucleotide sequence analysis. Subsequently, the ldhA gene was cloned as RcaI-XbaI fragment into pJS25 digested with NcoI-XbaI. The resulting expression vector, pJS26 (FIG. 5), has the ldhA gene of *L. bulgaricus* translationally fused to the *B. coagulans* promoter. Subsequently, the complete fragment encompassing the *B. coagulans* promoter and *L. delbrueckii* ldhA gene was transferred as a PstI-BglII fragment (by partial digestion with BglII) to the thermophilic cloning vector pNW33N digested with PstI-BamHI generating plasmid pJS27 (FIG. 6).

3) Overproduction of R-Lactate Dehydrogenase

Plasmid pJS27 was transformed to *B. coagulans* DSM 1 by electroporation. Specific R-lactate dehydrogenase enzyme activities were determined as decrease of absorbance at 340 nm per min per mg protein at 50° C. The specific activity of *B. coagulans* DSM 1 harbouring pNW33N was 0.45 ΔA min$^{-1}$ mg protein$^{-1}$ and that of *B. coagulans* DSM 1 harbouring pJS27 was 2.15 ΔA min$^{-1}$ mg protein$^{-1}$ demonstrating that the overproduction of R-lactate dehydrogenase in the modified strains containing the *L. delbrueckii* LMG 6901 ldhA gene resulted in a 4.8-times increased activity.

Example 5

Genetic Modification of *B. Coagulans* DSM 1 for R-Lactate Production

*B. coagulans* DSM 1 harbouring pJS27 (EXAMPLE 4) was grown in a batch culture mimicking industrial conditions. *B. coagulans* DSM 1 harbouring pNW33N and *B. coagulans* DSM 1 without plasmids were used as a reference strains. After fermentation the concentrations of organic acids and the optical purity of the lactic acid were determined (Table 2). Lactate produced by *B. coagulans* DSM 1 and *B. coagulans* DSM 1 harbouring pNW33N was enantiopure in the S-form, while the lactate produced by *B. coagulans* DSM 1 harbouring pJS27 was for a significant part in the R-form. No differences in by-product formation were detected. Concentrations of 2-hydroxy butyric acid, acetic acid, butyric acid, formic acid, pyruvic acid, were below the detection limits (<0.02% for pyruvic acid; <0.01% for others). Concentrations of succinic acid were below 0.1% (v/v). These results demonstrate that R-lactate production by *B. coagulans* can be achieved by introduction of an R-lactate dehydrogenase gene. Construction of a *B. coagulans* strain producing only R-lactate will require the disruption of the gene responsible for S-lactate dehydrogenase activity by random or site-directed mutagenesis.

TABLE 2

Organic acid production from 50 g/L sucrose (duplicate fermentations)

| | Glucose (g/L) | Lactic acid (g/L) | Chiral purity of S-lactic acid (S/R + S) * 100% | Chiral purity of R-lactic acid (R/S + R) * 100% |
|---|---|---|---|---|
| *B. coagulans* DSM 1 | <0.1 | 25/28 | 99.8/99.7 | 0.2/0.3 |
| *B. coagulans* DSM 1 + pNW33N | <0.1 | 25/22 | 99.8/99.7 | 0.2/0.3 |
| *B. coagulans* DSM 1 + pJS27 | <0.1 | 26/27 | 84.3/83.1 | 15.7/16.9 |

Example 6

Gene Replacement in *B. Coagulans* DSM 1 for Enantiopure R-Lactate Production

1) Construction of an Integration Plasmid

Figure 7:
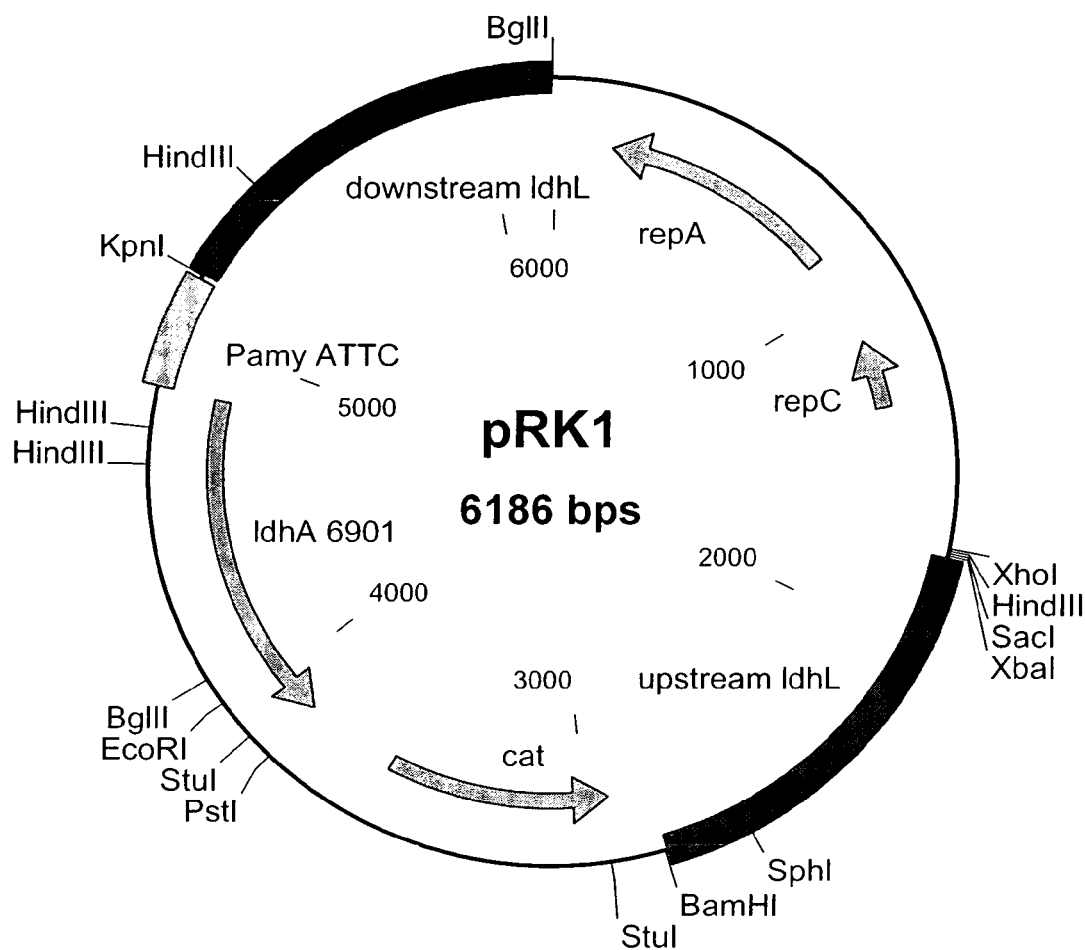
FIG. 7 shows a plasmid map of pRK1. The replication genes (repA and repC), the chloramphenicol resistance gene (cat), and the L. bulgaricus IdhA gene (IdhA) are depicted by arrows. The B. coagulans promoter region (Pamy ATTC) and B. coagulans IdhL upstream and downstream regions are depicted as boxed regions.

A modified *B. coagulans* strain producing R-lactate is constructed by replacing the *B. coagulans* ldhL gene coding for the major S-lactate dehydrogenase activity by the *L. bulgaricus* ldhA gene coding for R-lactate dehydrogenase. Replacement is achieved by homologous recombination in a two step process using a conditional cloning vector, e.g. a thermosensitive replicon which is functional at 45° C. but not at 55° C. We use the pSH71 replicon present in pNZ124 or pMH3, which was discovered to have such a thermosensitive nature in moderately thermophilic *Bacillus* species that are facultative anaerobic and homolactic. The integration vector pRK1 (FIG. 7) contains the pNZ124 replicon, two 1-kb regions flanking ldhL in the *B. coagulans* DSM 1 chromosome and now flanking the *B. coagulans* ATCC 23498 amy promoter fused to the *L. bulgaricus* ldhA gene and the cat gene encoding chloramphenicol resistance.

The integration vector is constructed by ligation of the following cassettes: (i) a 1.8-kb SalI-XbaI fragment, with the SalI site made blunt, containing the pNZ124 replicon; a 1.1-kb XbaI-BamHI fragment containing the upstream region of the ldhL gene cut from 4 PCR fragment generated using the primers 5'-GCGAGATCTAGAGGC-CATCTGGGGGGCTTTCT-3' (SEQ ID NO: 10) and 5'-CGCGGATCCATGGATAATCTTCCTC-CCCATCAAAAGTA-3' (SEQ ID NO: 11) and *B. coagulans* DSM 1 as a template; (iii) a 1.0-kb BamHI-PstI fragment containing the cat gene cut from a PCR fragment generated using the primers 5-CGCGGATCCCCTTCTTCAAC-TAACGGG-3' (SEQ ID NO: 12) and 5'-GCGCTGCAGT-TCGCTACGCTCAAATCC-3' (SEQ ID NO: 13) and pMH3 (EXAMPLE 4) as a template; (iv) a 1.3-kb PstI-KpnI fragment containing the *L. bulgaricus* LMG 6901 ldhA gene translationally fused to the *B. coagulans* ATCC 23498 amy promoter cut from pJS27 (EXAMPLE 5); (v) a 1.1-kb KpnI-BglII fragment, with the BglII site made blunt containing the downstream region of the ldhL gene cut from a PCR fragment generated using the primers 5'-CGCGGGTACCGGC-CGGGCTTTATGG-3' (SEQ ID NO: 11) and 5'-GCGCA-GATCTGTCGAGTAAACGCGGAAAGCATTG-3' (SEQ ID NO: 15) and *B. coagulans* DSM 1 as a template.

2) Exchange of the *B. Coagulans* DSM 1 IdhL Gene with the *L. Bulgaricus* LMG 6901 IdhA Gene Plasmid pRK1 is transformed to *B. coagulans* DSM 1 by electroporation. Transformants are obtained on BC plates supplemented with 7 mg/L chloramphenicol grown at 45° C. After confirmation of the transformation by plasmid isolation, a single colony is cultured in BC broth at 45° C. to mid log-phase after which the temperature is shifted to 55° C. and incubation is continued for 1 h. A dilution series is plated on BC plates and incubated overnight at 55° C. The colonies are pooled and plated on BC plates in a second dilution series. After overnight incubation at 55° C. colonies are tested for integration by PCR analysis confirming a single crossover event. One colony is selected for continued cultivation by sequential transfer of 1/1000 dilutions (approximately 10 generations) in BC broth with antibiotics at 55° C. After approximately 100 generations a dilution series is plated on BC plates with antibiotics. After overnight incubation at 55° C. colonies series are tested for the absence of the IdhL gene by colony PCR. Alternatively, a double crossover mutant can be screened for among the single crossover mutants of the first event by testing for the absence of the IdhL gene by colony PCR. Chromosomal DNA from a colony negative in these PCR reactions is isolated and further evaluated for the presence of IdhA and correct integration is confirmed by Southern blot analysis.

Example 7

Enantiopure R-Lactate Production with a Modified *B. Coagulans* DSM 1

1) Construction of Modified Strain

With the method described in EXAMPLE 6 a *B. coagulans* DSM 1 derivative was constructed with the ldhL gene replaced by a cassette containing the ldhA gene from an industrial *L. delbrueckii* strain fused to the ldhL promoter (SEQ ID NO: 16) from an industrial *B. coagulans* strain and the cat gene from pMH3. The resulting strain was designated RDSM 1.

2) Fermentation with RDSM 1

The RDSM 1 strain was grown in a batch culture mimicking industrial conditions. After fermentation the concentrations of organic acids and the optical purity of the lactic acid were determined (Table 3). Lactate produced by *B. coagulans* RDSM 1 was for 99.5% in the R-form. No differences in by-product formation were detected compared to *B. coagulans* DSM 1 (Example 5). Concentrations of 2-hydroxy butyric acid, acetic acid, butyric acid, formic acid, pyruvic acid, were below the detection limits (<0.02% for pyruvic acid; <0.01% for others). Concentrations of succinic acid were below 0.1% (v/v). These results demonstrate chromosomal deletion of native *B. coagulans* genes and chromosomal insertion and functional expression of (heterologous) genes is possible and can be applied for production of enantiopure R-lactate by *B. coagulans*.

TABLE 3

Organic acid production from 50 g/L sucrose (duplicate fermentations)

| | Glucose (g/L) | Lactic acid (g/L) | Chiral purity of S-lactic acid (S/R + S) * 100% | Chiral purity of R-lactic acid (R/S + R) * 100% |
| --- | --- | --- | --- | --- |
| *B. coagulans* DSM 1 | <0.1 | 25/28 | 99.8/99.7 | 0.2/0.3 |
| *B. coagulans* RDSM 1 | <0.1 | 27/28 | 0.5/0.5 | 99.5/99.5 |

The invention claimed is:

1. A method for modifying moderately thermophilic *Bacillus* species that are facultative anaerobic and homolactic by genetic engineering comprising:
   introducing a DNA cloned in a thermosensitive plasmid system containing a pSH71 replicon or a homologue of the replicon, wherein the homologue comprises a DNA sequence encoding a polypeptide having a thermosensitive replication functionality (the RepA protein) having an amino acid sequence that is at least 90% identical to SEQ ID NO: 1, into cells of a moderately thermophilic *Bacillus* species that is facultative anaerobic and homolactic;
   culturing the cells on a selective medium at a permissive temperature for plasmid replication to select transformed cells capable of growing on said selective medium at said permissive temperature; and
   culturing said transformed cells on a selective medium at a non-permissive temperature for plasmid replication to select transformed cells capable of growing on said selective medium at said non-permissive temperature.

2. The method according to claim 1, wherein the DNA provides a desired functionality.

3. The method according to claim 1, wherein the culturing at the non-permissive temperature for plasmid replication allows the DNA to be introduced into the chromosome of the *Bacillus* species.

4. The method according to claim 1, wherein an undesired functionality is removed from the *Bacillus* chromosome by homologous recombination.

5. The method according to claim 1, wherein a desired functionality is introduced in the *Bacillus* chromosome and simultaneously an undesired functionality is removed from the *Bacillus* chromosome by homologous recombination.

6. The method according to claim 5, wherein the *Bacillus* species is modified by replacing a gene encoding S-lactate dehydrogenase by a DNA construct comprising a DNA sequence encoding an amino acid sequence according to SEQ ID NO: 2 or an amino acid sequence homologous to SEQ ID NO: 2 having R-lactate dehydrogenase activity fused to a promoter functional in the *Bacillus* species.

7. The method according to claim 6, wherein the promoter is of the endogenous S-lactate dehydrogenase gene that is removed.

8. The method according to claim 1, wherein the *Bacillus* species are selected from the group consisting of *Bacillus smithii* and *Bacillus coagulans*.

9. The method according to claim 1, wherein the *Bacillus* species are sporulation deficient.

10. The method according to claim 3, wherein the culturing allows the DNA to be introduced into the chromosome of the *Bacillus* species by homologous recombination.

11. The method according to claim 8, wherein the *Bacillus* species is *Bacillus coagulans*.

* * * * *

SEQUENCE LISTING

```
<160> NUMBER OF SEQ ID NOS: 16

<210> SEQ ID NO 1
<211> LENGTH: 232
<212> TYPE: PRT
<213> ORGANISM: Plasmid pSH71

<400> SEQUENCE: 1

Met Ala Ile Lys Asn Thr Lys Ala Arg Asn Phe Gly Phe Leu Leu Tyr
1               5                   10                  15

Pro Asp Ser Ile Pro Asn Asp Trp Lys Glu Lys Leu Glu Ser Leu Gly
            20                  25                  30
```

```
Val Ser Met Ala Val Ser Pro Leu His Asp Met Asp Glu Lys Lys Asp
            35                  40                  45

Lys Asp Thr Trp Asn Ser Ser Asp Val Ile Arg Asn Gly Lys His Tyr
 50                  55                  60

Lys Lys Pro His Tyr His Val Ile Tyr Ile Ala Arg Asn Pro Val Thr
 65                  70                  75                  80

Ile Glu Ser Val Arg Asn Lys Ile Lys Arg Lys Leu Gly Asn Ser Ser
                 85                  90                  95

Val Ala His Val Glu Ile Leu Asp Tyr Ile Lys Gly Ser Tyr Glu Tyr
                100                 105                 110

Leu Thr His Glu Ser Lys Asp Ala Ile Ala Lys Asn Lys His Ile Tyr
                115                 120                 125

Asp Lys Lys Asp Ile Leu Asn Ile Asn Asp Phe Asp Ile Asp Arg Tyr
130                 135                 140

Ile Thr Leu Asp Glu Ser Gln Lys Arg Glu Leu Lys Asn Leu Leu Leu
145                 150                 155                 160

Asp Ile Val Asp Tyr Asn Leu Val Asn Thr Lys Asp Leu Met Ala
                165                 170                 175

Phe Ile Arg Leu Arg Gly Ala Glu Phe Gly Ile Leu Asn Thr Asn Asp
                180                 185                 190

Val Lys Asp Ile Val Ser Thr Asn Ser Ser Ala Phe Arg Leu Trp Phe
                195                 200                 205

Glu Gly Asn Tyr Gln Cys Gly Tyr Arg Ala Ser Tyr Ala Lys Val Leu
                210                 215                 220

Asp Ala Glu Thr Gly Glu Ile Lys
225                 230

<210> SEQ ID NO 2
<211> LENGTH: 333
<212> TYPE: PRT
<213> ORGANISM: Lactobacillus delbrueckii subsp. bulgaricus

<400> SEQUENCE: 2

Met Thr Lys Ile Phe Ala Tyr Ala Ile Arg Glu Asp Glu Lys Pro Phe
 1               5                  10                  15

Leu Lys Glu Trp Glu Asp Ala His Lys Asp Val Glu Val Glu Tyr Thr
                20                  25                  30

Asp Lys Leu Leu Thr Pro Glu Thr Val Ala Leu Ala Lys Gly Ala Asp
            35                  40                  45

Gly Val Val Val Tyr Gln Gln Leu Asp Tyr Thr Ala Glu Thr Leu Gln
 50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                 85                  90                  95

Thr Asn Val Pro Val Tyr Ser Pro Asn Ala Ile Ala Glu His Ala Ala
                100                 105                 110

Ile Gln Ala Ala Ile Leu Arg Gln Asp Lys Ala Met Asp Glu Lys
                115                 120                 125

Val Ala Arg His Asp Leu Arg Trp Ala Pro Thr Ile Gly Arg Glu Val
130                 135                 140

Arg Asp Gln Val Val Gly Val Ile Gly Thr Gly His Ile Gly Gln Val
145                 150                 155                 160

Phe Met Gln Ile Met Glu Gly Phe Gly Ala Lys Val Ile Thr Tyr Asp
                165                 170                 175
```

```
Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Glu Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Ile Phe Gly
            245                 250                 255

Tyr Ala Met Asp Val Tyr Glu Gly Glu Val Gly Ile Phe Asn Glu Asp
        260                 265                 270

Trp Glu Gly Lys Glu Phe Pro Asp Ala Arg Leu Ala Asp Leu Ile Ala
    275                 280                 285

Arg Pro Asn Val Leu Val Thr Pro His Thr Ala Phe Tyr Thr Thr His
290                 295                 300

Ala Val Arg Asn Met Val Val Lys Ala Phe Asp Asn Asn Leu Glu Leu
            305                 310                 315                 320

Val Glu Gly Lys Glu Ala Glu Thr Pro Val Lys Val Gly
            325                 330

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 3
tcgccttctt ctgtgtcatc                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 4
ctggaggaga gcaatgaaac                                                   20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct-primer

<400> SEQUENCE: 5
ctattattcc gtggacttc                                                    19

<210> SEQ ID NO 6
<211> LENGTH: 17
<212> TYPE: DNA
<213> ORGANISM: Artificial Sequence
<220> FEATURE:
<223> OTHER INFORMATION: Synthetic Construct-primer

<400> SEQUENCE: 6
cagctgagat cttggag                                                      17
```

-continued

```
<210> SEQ ID NO 7
<211> LENGTH: 25
<212> TYPE: DNA
<213> ORGANISM: Artificial Sequence
<220> FEATURE:
<223> OTHER INFORMATION: Synthetic Construct-primer

<400> SEQUENCE: 7
gacgaaagtc gacggcaata gttac                                         25

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct-primer

<400> SEQUENCE: 8
gacaattcat gactaaaatt tttgc                                         25

<210> SEQ ID NO 9
<211> LENGTH: 33
<212> TYPE: DNA
<213> ORGANISM: Artificial Sequence
<220> FEATURE:
<223> OTHER INFORMATION: Synthetic Construct-primer

<400> SEQUENCE: 9
ggatttctct agactgcagt tagccaacct taa                                33

<210> SEQ ID NO 10
<211> LENGTH: 32
<212> TYPE: DNA
<213> ORGANISM: Artificial Sequence
<220> FEATURE:
<223> OTHER INFORMATION: Synthetic Construct-primer

<400> SEQUENCE: 10
gcgagatcta gaggccatct gggggggcttt ct                                32

<210> SEQ ID NO 11
<211> LENGTH: 38
<212> TYPE: DNA
<213> ORGANISM: Artificial Sequence
<220> FEATURE:
<223> OTHER INFORMATION: Synthetic Construct-primer

<400> SEQUENCE: 11
cgcggatcca tggataatct tcctccccat caaaagta                           38

<210> SEQ ID NO 12
<211> LENGTH: 27
<212> TYPE: DNA
<213> ORGANISM: Artificial Sequence
<220> FEATURE:
<223> OTHER INFORMATION: Synthetic Contsruct-primer

<400> SEQUENCE: 12
cgcggatccc cttcttcaac taacggg                                       27

<210> SEQ ID NO 13
<211> LENGTH: 27
<212> TYPE: DNA
<213> ORGANISM: Artificial Sequence
<220> FEATURE:
<223> OTHER INFORMATION: Synthetic Construct-primer

<400> SEQUENCE: 13
```

```
gcgctgcagt tcgctacgct caaatcc                                                27
```

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct-primer

<400> SEQUENCE: 14

```
cgcgggtacc ggccgggctt tatgg                                                  25
```

<210> SEQ ID NO 15
<211> LENGTH: 34
<212> TYPE: DNA
<213> ORGANISM: Artificial Sequence
<220> FEATURE:
<223> OTHER INFORMATION: Synthetic Construct-primer

<400> SEQUENCE: 15

```
gcgcagatct gtcgagtaaa cgcggaaagc attg                                        34
```

<210> SEQ ID NO 16
<211> LENGTH: 304
<212> TYPE: DNA
<213> ORGANISM: Artificial Sequence
<220> FEATURE:
<223> OTHER INFORMATION: Synthetic Construct-promoter region

<400> SEQUENCE: 16

```
agatcttggt tccccacctt ttttacagac ttatcactat attattatag ataaaccggc            60
caaacaacca aatcggggcg caaaggagag ccggggcgtg gatttaaacc atttttggaa           120
aaacaaaagg aaaacctgct tgtaaaaaga tgttttcgcg aaacgaaagc gggaatagta           180
cctttgttct cttcgccttt tgtcatgctt aaaatcataa ttgattgaaa attttttcat           240
gttcacttat actaaacgca tcaactatta cttcttttgg aagggcagt ttccatgggg            300 atcc                                                                       304
```